(12) United States Patent
Verbeuren et al.

(10) Patent No.: US 7,618,955 B2
(45) Date of Patent: Nov. 17, 2009

(54) ASSOCIATION OF AN ANTITHROMBOTIC AND ASPIRIN

(75) Inventors: Tony Verbeuren, Vernouillet (FR); Gilbert Lavielle, La Celle Saint Cloud (FR); Bernard Cimetiere, Paris (FR); Marie-Odile Vallez, Champs sur Marne (FR)

(73) Assignee: Les Laboratoires Servier, Suresnes Cedex (FR)

( * ) Notice: Subject to any disclaimer, the term of this patent is extended or adjusted under 35 U.S.C. 154(b) by 601 days.

(21) Appl. No.: 10/509,605

(22) PCT Filed: Apr. 4, 2003

(86) PCT No.: PCT/FR03/01054

§ 371 (c)(1), (2), (4) Date: Sep. 27, 2004

(87) PCT Pub. No.: WO03/084525

PCT Pub. Date: Oct. 16, 2003

(65) Prior Publication Data

US 2005/0143354 A1 Jun. 30, 2005

(30) Foreign Application Priority Data

Apr. 5, 2002 (FR) .................................. 02 04222

(51) Int. Cl.
*A61K 31/60* (2006.01)
*A61K 31/195* (2006.01)

(52) U.S. Cl. .................. 514/165; 514/562; 560/143

(58) Field of Classification Search ................ 514/165, 514/562; 560/143
See application file for complete search history.

(56) References Cited

U.S. PATENT DOCUMENTS 5,472,979 A * 12/1995 Lavielle et al. .............. 514/562

FOREIGN PATENT DOCUMENTS

EP 0648741 4/1995

OTHER PUBLICATIONS

Helgason, et al., "Inhibition of Platelet aggregation by aspirin alone and by aspirin in combination with clopidogrel: synergy, incompatibility and additivity" IEEE, 2000, p. 215-217. http://ieeexplore.ieee.org/iel5/7041/18959/00877423.pdf.*

B. Cimetiere, et al., New Tetrahydronaphthalene derivatives as combined thromboxane receptor antagonists and thromboxane synthase inhibitors, Bioorganic & Medicinal Chemistry Letters, vol. 8, 1998, pp. 1381-1386.

B. Cimetiere, et al., "Synthesis and biological evaluation of new tetrahydronaphthalene derivatives as thromboxane receptor antagonists", Bioorganic & Medicinal Chemistry Letters, vol. 8, No. 11, Jun. 2, 1998, pp. 1375-1380.

S. Simonet, et al., "S 18886, A new thromboxane (TP)-receptor antagonist is the active isomer of S 18204 in all species, except in the Guinea-Pig", Advances in Experimental Medicine and Biology, vol. 433, 1997, pp. 173-176.

A. Cayatte, et al., "The thromboxane receptor antagonist S18886 but not aspirin inhibits atherogenesis in apo E-deficient mice: evidence that eicosanoids other than thromboxane contribute to atherosclerosis", Arteriosclerosis Thrombosis and Vascular Biology, vol. 20 No. 7, Jul. 2000, pp. 1742-1728.

* cited by examiner

*Primary Examiner*—Sreeni Padmanabhan
*Assistant Examiner*—Sahar Javanmard
(74) *Attorney, Agent, or Firm*—Hueschen and Sage

(57) ABSTRACT

The present invention relates to a new combination of an antithrombotic and aspirin and to pharmaceutical compositions comprising them.

6 Claims, No Drawings

ASSOCIATION OF AN ANTITHROMBOTIC AND ASPIRIN

The new invention relates to a new association of an antithrombotic and aspirin and to pharmaceutical compositions containing them.

More specifically, the present invention relates to the association of a TP receptor antagonist and aspirin.

Thromboxane $A_2$ ($TXA_2$) is an unstable metabolite of arachidonic acid which is involved in the pathogenesis of numerous disorders of blood circulation. Thromboxane $A_2$ is a powerful platelet activator but is also a powerful vasoconstrictor which has cell proliferative and pro-adhesive properties.

$TXA_2$ and other metabolites of arachidonic acid such as endoperoxide ($PGH_2$), HETEs and isoprostanes exert their action by way of common receptors called TP receptors.

Numerous research studies have recently been carried out with the aim of preventing circulatory disorders caused by the excessive production of thromboxane $A_2$. Among such antagonists, those described in the Patent Specification EP 648 741 have been found to be powerful and selective antagonists of TP receptors, to be active via the oral route and to have a long duration of action.

More specifically, the compound (A) of formula (I):

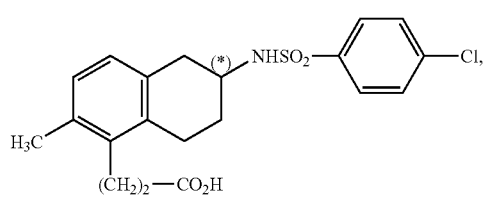

in racemic form or in the form of an optically pure isomer, and also pharmaceutically acceptable salts thereof, has been found to be a powerful antithrombotic.

That compound selectively inhibits blood platelet aggregation caused by activation of the TP receptors and, moreover, has anti-atherosclerotic properties after administration by the oral route.

We have now found that the association of compound A and aspirin allows, surprisingly, a synergy to be obtained in terms of antithrombotic activity.

It has been described in the literature that certain associations of anti-platelet aggregation agents such as dipyridamole and aspirin have additive effects and that such an association has been shown to be of value in the prevention of cerebral vascular accidents.

Other associations of anti-platelet aggregation agents with aspirin have been described in the literature. In view of the fact that those anti-aggregation agents act on platelet aggregation pathways (such as the purinergic pathways, ADP) which are different from those of aspirin, which acts via the pathway of arachidonic acid metabolism, it was expected that additive effects on the activity of those compounds would be observed.

The association to which the present invention relates is, for its part, completely different: compound A and aspirin both act on the arachidonic acid metabolism pathways: the former acts by irreversibly inhibiting the cyclo-oxygenases, which convert arachidonic acid into endoperoxide ($PGH_2$) and the latter acts by opposing the activity of certain metabolites of arachidonic acid such as thromboxane $A_2$, the isoprostanes and endoperoxide.

It has been found, surprisingly, that the association of compound A and aspirin allows substantial synergy to be obtained in terms of activity, which could not have been foreseen from any teaching of the literature.

That synergistic effect has been demonstrated in an arterial thrombosis test in the guinea-pig. In the course of that test it was shown that the antithrombotic activity of compound A is potentiated in the presence of aspirin and increases in extremely substantial and entirely unforeseeable manner.

In the associations according to the invention, compound (A) and aspirin can be present in the form of pharmaceutically acceptable salts.

Among the addition salts of compound (A), there may be mentioned, without implying any limitation, addition salts with a pharmaceutically acceptable base, such as sodium, potassium, tert-butylamine and diethylamine salts etc.

Preference will be given to use of the sodium salt.

Among the addition salts of aspirin, there may be mentioned, without implying any limitation, addition salts with a pharmaceutically acceptable acid, such as acetate, benzoate, fumarate, maleate, citrate, tartrate, the lysine salt etc.

In the associations according to the invention, compound (A) preferably has the absolute configuration (R).

The present invention relates also to pharmaceutical compositions comprising an association of compound (A) and aspirin, where appropriate in the form of pharmaceutically acceptable salts, together with one or more appropriate, inert, non-toxic excipients.

Among the pharmaceutical compositions according to the invention there may be mentioned more especially those that are suitable for oral, parenteral or nasal administration, tablets or dragees, sublingual tablets, gelatin capsules, lozenges, suppositories, creams, ointments, dermal gels etc.

The dosage can be varied according to the nature and severity of the condition, the administration route and also the age and weight of the patient.

In the compositions according to the invention, the amounts of active ingredients are in the range from 1 to 300 mg for compound (A) and from 100 to 1000 mg for aspirin.

The compositions according to the invention are accordingly useful in the treatment of atherothrombotic illnesses involving the activation of TP receptors and/or the formation of metabolites and also in the treatment of consequences of those illnesses. Those pathologies include, without implying any limitation, stable or unstable angina, endothelial or vascular dysfunction accompanying illnesses such as hypertension, diabetes, heart failure, disorders of the cardiovascular or cerebrovascular system, or thrombo-embolic disorders associated especially with atherosclerosis.

The associations according to the invention have been studied and the synergy effect has been demonstrated in an arterial thrombosis test in the guinea-pig.

This test is based on the model initially described by Roux et al. (Thromb Haemost 71: 252-256, 1994). The guinea-pigs are anaesthetised using ketamine+xylazine (90+12) mg.kg i.m. The trachea is cannulated and spontaneous respiration by the animals maintained. The jugular vein is cannulated, allowing the intravenous administration of the compounds being tested. The carotid artery is isolated, and a Doppler probe is installed allowing the arterial blood flow to be measured. After stabilisation, a lesion to the artery wall is produced by means of a clip applied distally to the Doppler probe. Subsequent to that lesion, the blood flow decreases. When the flow reaches zero, the artery is lightly shaken, which allows the flow to be restored. The thrombosis process continues, leading again to the flow reducing and ceasing. The thrombotic phenomena accordingly result in cyclic flow reductions (CFR), which are observed over a period of 20 minutes. After that period, the animal is treated, or not, with compound (A), and the CFR are again observed for a period of 20 minutes. The experiments are carried out in control animals or in animals treated by the intravenous route with aspirin (2 mg/kg).

This study was carried out using the sodium salt of the (R) isomer of compound (A).

The results show that 10±1 CFR/20 min are observed in the untreated animals. Compound (A), administered by the intravenous route, reduces the CFR in dose-dependent manner; a significant effect is obtained from the 0.3 mg/kg dose (5±2 CFR/20 min). Almost total inhibition (2±2 CFR/20 min) is obtained with a dose of 1 mg/kg.

In the animals treated with aspirin, 8±1 CFR/20 min are observed; that value is not different from that obtained in the control animals. Compound (A), administered by the intravenous route to animals already treated with aspirin, reduces the CFR in dose-dependant manner; a significant effect is now obtained from the 0.01 mg/kg dose (5±1 CFR/20 min), and almost complete inhibition is obtained with a dose of 0.1 mg/kg (2±1 CFR/20 min).

Those results firstly show the powerful antithrombotic activity of compound (A), which is active from the 0.3 mg/kg dose. Moreover, in the presence of a dose of aspirin which does not bring about an antithrombotic effect, the antithrombotic activity of compound (A) is potentiated and increased by at least 30 times. In fact, that effect is observed from the 0.01 mg/kg dose, which means that there exists a very substantial synergy effect when the two active ingredients are administered simultaneously.

The invention claimed is:

1. A composition comprising a combination of compound (A) of formula (I), optionally in the form of an optical isomer, or a pharmaceutically acceptable salt thereof, and aspirin, or a pharmaceutically acceptable salt thereof:

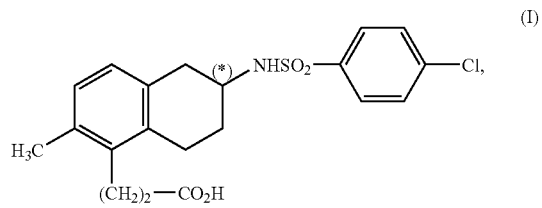

wherein compound (A) of formula (I), or an optical isomer or pharmaceutically acceptable salt thereof, is present in a range of from 1 to 300 mg, and aspirin, or a pharmaceutically acceptable salt thereof is present in a range of from 100 to 300 mg.

2. The composition of claim 1, wherein compound (A) has the (R) configuration.

3. The composition of claim 1, wherein compound (A) is in the form of a sodium salt.

4. A pharmaceutical composition comprising as active ingredients a combination of compound (A), optionally in the form of an optical isomer, or a pharmaceutically acceptable salt thereof, and aspirin, or a pharmaceutically acceptable salt thereof, wherein compound (A), or an optical isomer or pharmaceutically acceptable salt thereof, is present in a range of from 1 to 300 mg, and aspirin, or a pharmaceutically acceptable salt thereof is present in a range of from 100 to 300 mg, in combination with one or more pharmaceutically acceptable, inert excipients or carriers.

5. The pharmaceutical composition of claim 4, wherein compound (A) has the (R) configuration.

6. The pharmaceutical composition of claim 4, wherein compound (A) is in the form of a sodium salt.

* * * * *